United States Patent [19]

Walker

[11] Patent Number: 5,071,852
[45] Date of Patent: Dec. 10, 1991

[54] DERIVATIVES OF 5-HYDROXY AND 5-METHOXY 2-AMINO-PYRIMIDINES AS INHIBITORS OF INTERLEUKIN-1 PRODUCTION

[75] Inventor: Frederick J. Walker, Preston, Conn.

[73] Assignee: Pfizer Inc., New York, N.Y.

[21] Appl. No.: 444,653

[22] Filed: Dec. 1, 1989

Related U.S. Application Data

[63] Continuation-in-part of Ser. No. 284,505, Dec. 14, 1988, abandoned.

[51] Int. Cl.$^5$ ............................................ A61K 31/505
[52] U.S. Cl. .................................... 514/272; 514/900
[58] Field of Search ......................... 514/272, 273, 900

[56] References Cited

U.S. PATENT DOCUMENTS

| 4,554,276 | 11/1985 | LaMattina | 514/272 |
| 4,673,677 | 6/1987 | LaMattina | 514/272 |
| 4,677,132 | 6/1987 | Hayward | 514/411 |
| 4,711,888 | 12/1987 | Walker et al. | 514/269 |
| 4,780,470 | 10/1988 | Bender et al. | 514/341 |

FOREIGN PATENT DOCUMENTS

8704618 8/1987 PCT Int'l Appl. .

OTHER PUBLICATIONS

Hayward, M. et al., "Mechanisms of Bone Loss: Rheumatoid Arthritis, Periodontal Disease and Osteoporosis", Agents and Actions, 22, 251–254 (1987).
Hayward, M. et al., Annual Reports in Medicinal Chemistry, 22, Sect. IV, Chapter 17, pp. 172–177 (1987).
Dinarello, C. A., "An Update on Human Interleukin-1: From Molecular Biology to Clinical Relevance", J. Clin. Immunol., 5, 287–297 (1985).
Camp, R. D. et al., "Psoriatic Skin Lesions Contain Biologically Active Amounts of an Interleukin-1-Like Compound", J. Immunol., 13 3469–3474 (1986).
Dinarello, C. A., "Biology of Interleukin 1", FASEB J., 2, 108–115 (1988).
Essner, R. et al., "Inhibition of Human Peripheral Monocyte Interleukin-1(IL-1) Production by Lipoxygenase Antagonists", Proceedings of AACR 29 (Mar. 1988), No. 1485.
Kunkel, S. L. et al., "Arachidonic-Acid Metabolites Regulate Interleukin 1 Production", Biochem. Biophys. Res. Commun. 128:892–897 (1985).
Smith, R.J. et al., "Human Neutrophil Activation with Interleukin 1-A Role for Intracellular Calcium and Arachidonic Acid Lipoxygenation", Biochem. Pharmacol. 36:3851–3858 (1987).
Dinarello, C. A. et al., "Role of Arachidonate Metabolism in the Immunoregulatory Function of Human Leukocytic Pyrogen/Lymphocyte-Activating Factor/Interleukin 1", J. Immunol., 130, 890–895 (1983).
Dinarello, C. A. et al., "The Influence of Lipoxygenase Inhibitors on the In Vitro Production of Human Leukocytic Pyrogen and Lymphocyte Activating Factor (Interleukin-1)", Int. J. Immunopharmac., 6, 43–50 (1984).
McDonald, B. et al., "The Influence of a Novel Arachidonate Inhibitor, CP-66,248 on the Production and Activity of Human Monocyte IL-1", Arthritis Rheum. 34 (4 Suppl.):S17 (1988).
Otterness, I. G. et al., "Effects of CP-66,248 on IL-1 Synthesis by Murine Peritoneal Macrophages", Arthritis Rheum. 34 (4 Suppl.):S90 (1988).
Meikle et al., Chem. Abstracts 105(19): 169829z (1986).

*Primary Examiner*—Frederick E. Waddell
*Assistant Examiner*—Raymond J. Henley, III
*Attorney, Agent, or Firm*—Peter C. Richardson; J. Trevor Lumb; Gregg C. Benson

[57] ABSTRACT

This invention relates to the use of certain derivatives of 5-hydroxy and 5-methoxy 2-aminopyrimidines of the formula

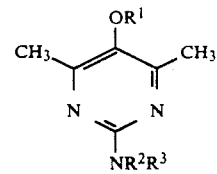

and the pharmaceutically-acceptable salts thereof, wherein $R^1$ is H or $CH_3$; $R^2$ is $(C_3-C_{15})$ straight chain alkyl or $(C_7-C_{20})$phenylalkyl which may be substituted in the phenyl by one or two fluoro or chloro substituents; and $R^3$ is H or $CH_3$ to inhibit interleukin-1 production in a mammal. This invention also relates to the use of such compounds for treating interleukin-1 mediated disorders and dysfunctions such as bone and connective tissue metabolism disorders and immune dysfunction in a mammal. The methods of this invention comprise administering an interleukin-1 production inhibiting amount of the compounds and salts of this invention to such a mammal.

35 Claims, No Drawings

DERIVATIVES OF 5-HYDROXY AND 5-METHOXY 2-AMINO-PYRIMIDINES AS INHIBITORS OF INTERLEUKIN-1 PRODUCTION

CROSS REFERENCE TO RELATED APPLICATION

This application is a continuation-in-part of application Ser. No. 07/284,505, filed Dec. 14, 1988, now abandoned.

BACKGROUND OF THE INVENTION

1. Field of the Invention

This invention relates to the use of certain derivatives of 5-hydroxy and 5-methoxy 2-aminopyrimidines and the pharmaceutically-acceptable salts thereof to inhibit interleukin-1 production in a mammal. This invention also relates to the use of such compounds for treating interleukin-1 mediated disorders and dysfunctions such as bone and connective tissue metabolism disorders and immune dysfunction in a mammal. The methods of this invention comprise administering an effective amount of the compounds and salts of this invention to such a mammal.

2. General Background

Certain 5-hydroxy and 5-alkoxy pyrimidines of the formula

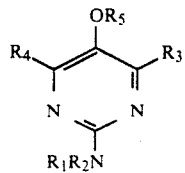

and the pharmaceutically-acceptable salts thereof wherein, inter alia, $R_1$ is H; $R_2$ is H, $(C_1-C_{15})$alkyl or $(C_7-C_{20})$phenylalkyl which may be substituted in the phenyl by one or two of fluoro or chloro; $R_3$ is $(C_1-C_6)$alkyl; $R_4$ is H or $(C_1-C_6)$alkyl; and $R_5$ is H or $(C_1-C_6)$alkyl are disclosed and claimed in U.S. Pat. No. 4,711,888 which is assigned to the assignee hereof. That patent discloses that those compounds are inhibitors of leukotriene synthesis and are useful for the treatment of pulmonary, inflammatory, allergic and cardiovascular diseases as well as being cytoprotective and, therefore, useful in the treatment of peptic ulcers. Specific utilities disclosed for those compounds include treatment of asthma, bronchitis, pulmonary diseases, such as pulmonary hypertension and hypoxia, peptic ulcers, psoriasis, arthritis, inflammatory bowel disease or cardiovascular spasm, such as acute myocardial infarctions. The teachings thereof are incorporated herein by reference.

Certain 2-amino-5-hydroxy-4-methyl pyrimidine derivatives of the formula

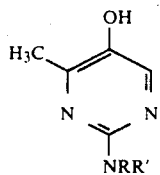

and the pharmaceutically-acceptable acid addition salts thereof wherein, inter alia, R is H or $(C_1-C_{15})$alkyl and R' is $(C_1-C_{15})$alkyl are disclosed and claimed in U.S. Pat. No. 4,554,276 which is assigned to the assignee hereof. That patent discloses that those compounds are inhibitors of leukotriene synthesis and are useful in the treatment of pulmonary, inflammatory and cardiovascular diseases, cancer and psoriasis. Further, those compounds are disclosed as having cytoprotective activity and therefore are also useful in the treatment of peptic ulcers. A method of treating gastrointestinal disorders with compounds disclosed in U.S. Pat. No. 4,554,276 discussed above is disclosed and claimed in U.S. Pat. No. 4,673,677. Both U.S. Pat. No. 4,554,276 and U.S. Pat. No. 4,673,677 are assigned to the assignee hereof and the teachings thereof are incorporated herein by reference.

Interleukin-1 (IL-1) has been reported to stimulate bone resorption both in vitro and in vivo. Hayward, M. and Fiedler-Nagy, Ch., Agents and Actions, 22, 251–254 (1987). It is also reported therein that IL-1, inter alia, induces the production of prostaglandin $E_2$ ($PGE_2$) $PGE_2$ is a stimulator of bone resorption and has been implicated in bone loss. Hayward, M. A. and Caggiano, T. J., Annual Reports in Medicinal Chemistry, 22, Sect. IV, Chapter 17, 172–177 (1987). Osteoporosis is defined as a debilitory loss of bone mineral which results in higher fracture rates. See Hayward, M. A. and Caggiano, T. J., supra and references cited therein.

Interleukin-1 has been reported to be involved in the pathogenesis of many diseases. See Dinarello, C. A., J. Clin. Immunol., 5, 287–297 (1985), the teachings of which are incorporated herein by reference. Further still, elevated levels of IL-1 like material have been found to be associated with psoriasis. Camp, R. D., et al., J. Immunol., 137, 3469–3474 (1986).

The non-steroidal anti-inflammatory agent etodolac, 1,8-diethyl-1,3,4,9-tetrahydropyrano[3,4-b] indole-1-acetic acid, has been disclosed in U.S. Pat. No. 4,677,132 to lower $PGE_2$ and reduce bone resorption. Etodolac has the formula

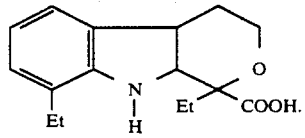

It has been reported that therapeutic levels of nonsteroidal anti-inflammatory agents such as indomethacin and ibuprofen do not reduce IL-1 production. Similarly, cyclosporine A had no such effect. Corticosteroids, however, are effective in reducing IL-1 production. Dinarello, C. A., supra. Certain lipoxygenase inhibitors such as 5,8,11,14-eicosatetraynoic acid (ETYA) and 3-amino-1,3-trifluoromethylphenyl-2-pyrazoline (BW755C) have been reported to decrease in vitro production of leukocytic pyrogen (putative IL-1) from human monocytes. Dinarello, C. A., et al., Int. J. Immunopharmac., 6, 43–50 (1984).

However, until the invention herein, there was no report of use or intent to use the compounds or salts of this invention to inhibit IL-1 production and to treat IL-1 mediated disorders and dysfunctions such as certain bone and connective tissue metabolism disorders and certain immune dysfunctions with such compounds nor any appreciation of their role in such treatments.

SUMMARY OF THE INVENTION

It has been found that certain 5-hydroxy and 5-methoxy pyrimidines of the formula

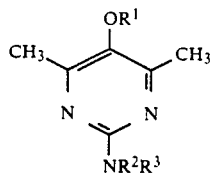

and the pharmaceutically-acceptable salts thereof wherein $R^1$ is H or $CH_3$; $R^2$ is ($C_3$-$C_{15}$) straight chain alkyl or ($C_7$-$C_{20}$) phenylalkyl which may be substituted in the phenyl by one or two fluoro or chloro substituents; and $R^3$ is H or $CH_3$ inhibit the production of IL-1 and thus are useful in treating IL-1 mediated disorders and dysfunctions such as certain disorders of bone and connective tissue metabolism and dysfunctions of the autoimmune system in mammals. Such bone metabolism disorders include, but are not limited to osteoporosis. By way of example and not of limitation, such connective tissue metabolism disorders include periodontal disease and tissue scarring. Further, examples of IL-1 mediated immune dysfunctions include, but are not limited to, allergy and psoriasis.

The methods of using the compounds and their pharmaceutically-acceptable base salts comprise administering to a mammal an effective amount of such compounds. Administration can comprise any known method for therapeutically providing a compound to a mammal such as by oral or parenteral administration a defined hereinbelow.

DETAILED DESCRIPTION OF THE INVENTION

The compounds of this invention which are of the formula

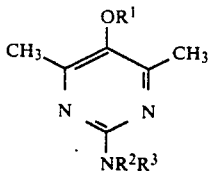

and the pharmaceutically-acceptable salts thereof wherein $R^1$ is H or $CH_3$; $R^2$ is ($C_3$-$C_{15}$) straight chain alkyl or ($C_7$-$C_{20}$)phenylalkyl which may be substituted in the phenyl by one or two fluoro or chloro substituents; and $R^3$ is H or $CH_3$ and the preparation thereof are disclosed in U.S. Pat. No. 4,554,276 and U.S. Pat. No. 4,711,888, the teachings of which are incorporated herein by reference. This invention concerns new uses for such compounds which comprise methods for inhibiting interleukin-1 (IL-1) production in a mammal. Also within the scope of this invention are methods of treating interleukin-1 mediated disorders and dysfunctions such as bone and connective tissue metabolism disorders and immune dysfunction.

Of the methods described above, preferred therein are those where the compound employed is of the formula above wherein $R^1$ is H; $R^2$ is $(CH_2)_8CH_3$ or $(CH_2)_6C_6H_5$ and $R^3$ is H; and those wherein in said compound $R^1$ is $CH_3$; $R^2$ is $(CH_2)_6C_6H_5$; and $R^4$ is $CH_3$.

Particularly preferred are methods wherein in said compound $R^1$ is H; $R^2$ is $(CH_2)_6C_6H_5$; and $R^3$ is H.

As disclosed in U.S. Pat. No. 4,554,276 and U.S. Pat. No. 4,711,888 the compounds of this invention hereinabove described will form pharmaceutically-acceptable salts. All such pharmaceutically-acceptable salts are within the scope of this invention and can be formed as taught by those patents. Such suitable salts, within the scope of this invention, include both the organic and inorganic types. Preferred acid addition salts are those of acetic, ascorbic, lactic, sulfonic, hydrobromic, hydroiodic and hydrochloric. Particularly preferred are the salts of sodium where $R^1$ is H; hydrochloride; phosphate; and tartrate.

Interleukin-1 is known by those skilled in the art to exist in at least two forms which are referred to as the $\alpha$ and $\beta$ forms. Dinarello, C. A., FASEB J., 2, 108-115 (1988). As used throughout this specification and the appendant claims, the term interleukin-1 (IL-1) refers to all such forms of IL-1 including IL-1$\alpha$, IL-1$\beta$ and Il-1$\alpha$ and IL-1$\beta$ collectively.

The methods of this invention comprise administering the invention compounds and the pharmaceutically-acceptable salts thereof to a mammal. Such compounds and their salts can be administered to said mammal either alone or, preferably, in combination with pharmaceutically-acceptable carriers or diluents in a pharmaceutical composition, according to standard pharmaceutical practice. Such administration can be oral or parenteral. Parenteral administration as used herein includes, but is not limited to, intravenous, intramuscular, intraperitoneal, subcutaneous, transdermal, transmucosal and topical including, but not limited to, oral lavage administration. However, it is generally preferred to administer such compounds and their salts, in the methods of this invention, topically.

In general, these compounds and their salts are most desirably administered in doses ranging from about 0.01 mg up to about 100 mg/kg body weight of the subject to be treated per day, although variations will still necessarily occur depending upon the subject being treated. The appropriate dose for inhibiting IL-1 production in a mammal and for treatment of IL-1 mediated bone metabolism disorder, IL-1 mediated connective tissue metabolism disorder or IL-1 mediated immune dysfunction with the compounds and their salts of this invention will be readily determined by those skilled in the art of prescribing and/or administering such compounds. Nevertheless, it is still to be appreciated that other variations may also occur in this respect, depending upon the species of mammal being treated and its individual response to said medicament, as well as on the particular type of pharmaceutical formulation chosen and the time period and interval at which such administration is carried out. In some instances, dosage levels below the lower limit of the aforesaid range may be more than adequate, while in other cases still larger doses may be employed without causing any harmful or deleterious side effects to occur, provided that such higher dose levels are first divided into several smaller doses that are to be administered throughout the day.

For purposes of oral administration, tablets containing excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as, but not limited to, magnesium stearate, sodium lauryl sulfate and talc are often very useful for tableting purposes. Solid compositions of a similar type may also be employed as fillers in soft elastic and hard-filled gelatin capsules; preferred materials in this connection also include, by way of example and not of limitation, lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with diluents such as water, ethanol, propylene glycol, glycerin and various like combinations thereof.

Although the preferred mode of administration of the compounds of this invention and their pharmaceutically-acceptable salts is oral, they may be administered parenterally as well.

For purposes of parenteral administration, solutions of these particular compounds in sesame or peanut oil or in aqueous propylene glycol may be employed, as well as sterile aqueous solutions of the corresponding water soluble salts thereof. Such aqueous solutions should be suitably buffered, if necessary, and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter such as a sintered glass filter or a diatomaceous-earth or unglazed porcelain filter. Preferred filters of this type include the Berkefeld, the Chamberland and the Asbestos Disk-Metal Seitz filter, wherein the fluid is sucked into a sterile container with the aid of a suction pump. Of course, the necessary steps should be taken throughout the preparation of these injectable solutions to insure that the final products are obtained in a sterile condition. For purposes of transdermal administration, the dosage form of the particular compound may include, by way of example, solutions, lotions, ointments, creams, gels, suppositories, rate-limiting sustained release formulations and devices therefor. Such dosage forms comprise the particular compound and may include ethanol, water, penetration enhancer and inert carriers such as gel-producing materials, mineral oil, emulsifying agents, benzyl alcohol and the like. Specific transdermal flux enhancing compositions are disclosed in European Patent Application, publication number 271983, published June 22, 1988 and in pending U.S. patent application Ser. No. 161,926, filed Feb. 29, 1988, both of which are assigned to the assignee of this invention, the teachings of which are incorporated herein by reference. For purposes of topical administration, the dosage form of the particular compound may include, by way of example and not of limitation, solutions, lotions, ointments, creams and gels.

The ability of the compounds of this invention to inhibit interleukin-1 biosynthesis is demonstrated by the assay procedures described below.

THP-1 cells [ATCC TIB 202; Int. J. Cancer 26:171 (1980); Cancer Res. 42:15230 (1982); J. Immunol. 131:1882 (1983); Biochemistry 25:2424 (1986)] are maintained in RPMI medium (Hazelton Research Products, Inc., Lenexa, Kans.) with 10% fetal bovine serum, 2 mM glutamine, 100 $\mu$/ml penicillin and 100 $\mu$g/ml streptomycin at 37° C. under an atmosphere of 95% oxygen and 5% carbon dioxide. The compound under study is dissolved initially in DMSO and diluted to a final concentration of 1% DMSO in RPMI. A known concentration of the compound prepared as described above is added in a volume of 0.25 ml to a well of a 24-well multicluster tissue culture plate. The THP-1 cells maintained as described above are harvested by centrifugation in 50 ml conical tubes at 500×g and room temperature. The resulting cell pellet is resuspended and washed twice with serum free RPMI containing glutamine and antibiotics as described above. The cells are suspended to a final density of 2×10$^6$ cells/ml. Then, fetal bovine serum is added to the cell suspension to a final concentration of 0.65 weight percent. The THP-1 cells are then stimulated with lipopolysaccharide (LPS) from *Salmonella minnesota* and silica by adding LPS and silica from stock solutions of each, prepared at 1 mg/ml in RPMI, to a final concentration of 13 $\mu$g/ml for each. A volume of 0.75 ml of the stimulated cell suspension is added to each well of the multicluster tissue culture plate containing a solution of the compound under study or RPMI medium as a control. The plates are mixed and incubated at 37° C. for 24 hours under an atmosphere of 95% oxygen and 5% carbon dioxide. After incubation, the medium from each well is centrifuged separately at 1500×g and the supernatants recovered. The supernatants are then assayed for IL-1$\beta$ immediately or, if not, stored at −70° C. until assayed. The IL-1$\beta$ concentration in the medium is determined by a sandwich ELISA system obtained from Cistron Biotechnology (10 Bloomfield Avenue, Line Brook, N.J. 07058) according to the procedure specified by the manufacturer. The resulting color reaction of the conjugated horseradish peroxidase enzyme conversion of o-phenylenediame to o-quinone is read at 490 nm on an ELISA plate reader and is proportional to the amount of IL-1$\beta$ present in the sample as determined from a standard curve using an IL-1$\beta$ standard and is expressed in pg/ml.

What is claimed is:

1. A method of inhibiting interleukin-1 production in a mammal in need thereof which comprises administering to said mammal an interleukin-1 production inhibiting amount of a compound of the formula

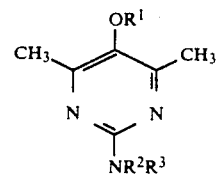

or a pharmaceutically-acceptable salt thereof, wherein $R^1$ is H or $CH_3$; $R^2$ is ($C_9$-$C_{12}$) straight chain alkyl or ($C_9$-$C_{12}$) phenylalkyl which may be substituted in the phenyl by one chloro substituent; and $R^3$ is H or $CH_3$.

2. The method according to claim 1 wherein $R^1$ is H.

3. The method according to claim 1 wherein $R^1$ is $CH_3$.

4. The method according to claim 2 wherein $R^2$ is $(CH_2)_6C_6H_5$; and $R^3$ is H.

5. The method according to claim 2 wherein $R^2$ is $(CH_2)_8CH_3$; and $R^3$ is H.

6. The method according to claim 3 wherein $R^2$ is $(CH_2)_6C_6H_5$; and $R^3$ is $CH_3$.

7. The method according to claim 1 wherein the compound or a pharmaceutically-acceptable salt thereof is administered orally.

8. The method according to claim 1 wherein the compound or a pharmaceutically-acceptable salt thereof is administered parenterally.

9. A method of treating interleukin-1 mediated bone metabolism disorders in a mammal in need thereof which comprises administering to said mammal an interleukin-1 mediated bone metabolism disorder treating amount of a compound of the formula

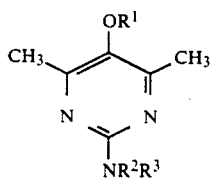

or a pharmaceutically-acceptable salt thereof, wherein $R^1$ is H or $CH_3$; $R^2$ is $(C_9-C_{12})$ straight chain alkyl or $(C_9-C_{12})$phenylalkyl which may be substituted in the phenyl by one chloro substituent; and $R^3$ is H or $CH_3$.

10. The method according to claim 9 wherein $R^1$ is H.

11. The method according to claim 9 wherein $R^1$ is $CH_3$.

12. The method according to claim 10 wherein $R^2$ is $(CH_2)_6C_6H_5$; and $R^3$ is H.

13. The method according to claim 10 wherein $R^2$ is $(CH_2)_8CH_3$; and $R^3$ is H.

14. The method according to claim 11 wherein $R^2$ is $(CH_2)_6C_6H_5$; and $R^3$ is $CH_3$.

15. The method according to claim 9 wherein the compound or a pharmaceutically-acceptable salt thereof is administered orally.

16. The method according to claim 9 wherein the compound or a pharmaceutically-acceptable salt thereof is administered parenterally.

17. The method according to claim 9 wherein the bone metabolism disorder is osteoporosis.

18. A method of treating interleukin-1 mediated connective tissue metabolism disorders in a mammal in need thereof which comprises administering to said mammal an interleukin-1 mediated connective tissue metabolism disorder treating amount of a compound of the formula

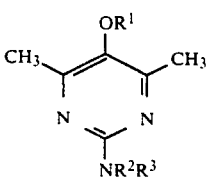

or a pharmaceutically-acceptable salt thereof, wherein $R^1$ is H or $CH_3$; $R^2$ is $(C_9-C_{12})$ straight chain alkyl or $(C_9-C_{12})$phenylalkyl which may be substituted in the phenyl by one chloro substituent; and $R^3$ is H or $CH_3$.

19. The method according to claim 18 wherein $R^1$ is H.

20. The method according to claim 18 wherein $R^1$ is $CH_3$.

21. The method according to claim 19 wherein $R^2$ is $(CH_2)_6C_6H_5$; and $R^3$ is H.

22. The method according to claim 19 wherein $R^2$ is $(CH_2)_8CH_3$; and $R^3$ is H.

23. The method according to claim 20 wherein $R^2$ is $(CH_2)_6C_6H_5$; and $R^3$ is $CH_3$.

24. The method according to claim 18 wherein the compound or a pharmaceutically-acceptable salt thereof is administered orally.

25. The method according to claim 18 wherein the compound or a pharmaceutically-acceptable salt thereof is administered parenterally.

26. The method according to claim 18 wherein the connective tissue metabolism disorder is periodontal disease.

27. The method according to claim 18 wherein the connective tissue metabolism disorder is tissue scarring.

28. A method of treating interleukin-1 mediated immune dysfunction in a mammal in need thereof which comprises administering to said mammal an interleukin-1 mediated immune dysfunction treating amount of a compound of the formula

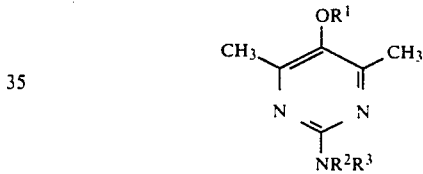

or a pharmaceutically-acceptable salt thereof, wherein $R^1$ is H or $CH_3$; $R^2$ is $(C_9-C_{12})$ straight chain alkyl or $(C_9-C_{12})$phenylalkyl which may be substituted in the phenyl by one chloro substituent; and $R^3$ is H or $CH_3$.

29. The method according to claim 28 wherein $R^1$ is H.

30. The method according to claim 28 wherein $R^1$ is $CH_3$.

31. The method according to claim 29 wherein $R^2$ is $(CH_2)_6C_6H_5$; and $R^3$ is H.

32. The method according to claim 29 wherein $R^2$ is $(CH_2)_8CH_3$; and $R^3$ is H.

33. The method according to claim 30 wherein $R^2$ is $(CH_2)_6C_6H_5$; and $R^3$ is $CH_3$.

34. The method according to claim 28 wherein the compound or a pharmaceutically-acceptable salt thereof is administered orally.

35. The method according to claim 28 wherein the compound or a pharmaceutically-acceptable salt thereof is administered parenterally.

* * * * *